(12) United States Patent
Hagiwara

(10) Patent No.: US 7,946,991 B2
(45) Date of Patent: May 24, 2011

(54) ULTRASONIC DOPPLER BLOOD FLOW MEASURING DEVICE

(75) Inventor: Hisashi Hagiwara, Kanagawa (JP)

(73) Assignee: Panasonic Corporation, Osaka (JP)

( * ) Notice: Subject to any disclaimer, the term of this patent is extended or adjusted under 35 U.S.C. 154(b) by 461 days.

(21) Appl. No.: 10/572,428

(22) PCT Filed: Oct. 15, 2004

(86) PCT No.: PCT/JP2004/015289
§ 371 (c)(1),
(2), (4) Date: Dec. 1, 2006

(87) PCT Pub. No.: WO2005/037104
PCT Pub. Date: Apr. 28, 2005

(65) Prior Publication Data
US 2007/0161900 A1 Jul. 12, 2007

(30) Foreign Application Priority Data
Oct. 17, 2003 (JP) .................................. 2003-358059

(51) Int. Cl.
*A61B 8/00* (2006.01)
(52) U.S. Cl. ......... 600/455; 600/454; 600/457; 600/453
(58) Field of Classification Search .................. 600/453, 600/454, 455, 456, 457, 407, 437
See application file for complete search history.

(56) References Cited

U.S. PATENT DOCUMENTS

| | | | |
|---|---|---|---|
| 4,799,490 A | * | 1/1989 | Namekawa .................... 600/455 |
| 5,107,466 A | * | 4/1992 | Nishiyama et al. ............. 367/90 |
| 5,188,113 A | * | 2/1993 | Sato et al. ...................... 600/455 |
| 5,231,573 A | * | 7/1993 | Takamizawa ................. 600/437 |

(Continued)

FOREIGN PATENT DOCUMENTS

JP 04-161146. 6/1992

(Continued)

OTHER PUBLICATIONS

Supplementary European Search Report dated Mar. 10, 2008.

*Primary Examiner* — Tse Chen
*Assistant Examiner* — Joel F Brutus
(74) *Attorney, Agent, or Firm* — Pearne & Gordon LLP

(57) ABSTRACT

A technology for performing the filter processing of blood flow velocity data having aliasing by only common filter processing means and common addition and subtraction means and actualizing image display of smooth blood flow velocity is disclosed. According to this technology, when performing image display of the blood flow velocity of blood within a subject biological body using an ultrasonic wave Doppler method, the difference values of data D33 of an arbitrary focus point and data D32 and D34 of points spatially prior and subsequent to this focus point are calculated in the pre-processing unit (difference calculating unit) 41. Then, in the filtering unit 42, after filter processing is performed on these difference values, data D39 after filter processing and data D33 of the arbitrary focus point are added in the post-processing unit (addition processing unit) 43. In this way, a filter processing can be performed under the assumption that the velocity difference is smaller than the velocity difference generated by the aliasing phenomenon, and filter processing of the blood flow velocity value in the sound ray direction of the ultrasonic waves can be performed without being influenced by aliasing.

3 Claims, 5 Drawing Sheets

U.S. PATENT DOCUMENTS

| | | | |
|---|---|---|---|
| 5,453,575 A * | 9/1995 | O'Donnell et al. | 600/463 |
| 5,609,155 A * | 3/1997 | Guracar | 600/453 |
| 5,622,174 A * | 4/1997 | Yamazaki | 600/441 |
| 5,828,444 A * | 10/1998 | Nomura | 356/28 |
| 6,077,226 A | 6/2000 | Washburn et al. | |
| 6,547,731 B1 | 4/2003 | Coleman et al. | |
| 6,599,248 B1 | 7/2003 | Tamura | |

FOREIGN PATENT DOCUMENTS

| | | |
|---|---|---|
| JP | 05-095948 | 4/1993 |
| JP | 05-212032 | 8/1993 |
| JP | 07-016226 | 1/1995 |
| JP | 10-099332 | 4/1998 |
| JP | 2000-126179 | 5/2000 |

* cited by examiner

ULTRASONIC DOPPLER BLOOD FLOW MEASURING DEVICE

TECHNICAL FIELD

The present invention relates to an ultrasonic Doppler blood flow measuring device which measures blood flow within a biological body by using the Doppler phenomenon of ultrasonic waves and performs image display regarding the measured results, in the medical field, and more particularly, relates to an ultrasonic Doppler blood flow measuring device for showing, by color display, an image according to the blood flow rate data generated by the aliasing phenomenon.

BACKGROUND ART

Conventionally, an ultrasonic Doppler blood flow measuring device (color flow device), which enables measurement of blood flow distribution and blood flow velocity within a biological body by using the Doppler phenomenon of ultrasonic waves and displays the blood flow velocity, in correspondence to a predetermined color, by superimposing a black and white, two-dimensional cross-sectional image therewith, is known.

FIG. 5 is a block diagram of an example of a configuration of an ultrasonic Doppler blood flow measuring device according to prior art. The ultrasonic Doppler blood flow measuring device has a probe 2 for performing transmission and reception of ultrasonic waves to a biological body. An ultrasonic pulse is irradiated from a transmitting unit 1 to the blood flowing within the biological body, and the probe 2 again receives an echo of the ultrasonic pulse reflected by the blood. The echo of the ultrasonic pulse is converted into an electrical signal by the probe 2 and supplied to a receiving unit 3. After digitalization or beamforming by the receiving unit 3, the signal is phase-detected by a phase detecting unit 4 and becomes a Doppler-shift signal comprising information on the Doppler-shift due to blood flow.

The Doppler-shift signal is supplied from the phase detecting unit 4 to a wall filter 5. In wall filter 5, signals from unnecessary tissues which are low-frequency signal components are removed, and furthermore, in a velocity calculating unit 6, blood flow information, such as blood flow velocity data, blood echo intensity data, blood flow velocity variance data, and the like, is determined based on the signal subsequent to processing by the wall filter 5. This blood flow information is smoothing-processed by a filter 7, supplied to a digital scan Converter (DSC) 8, and coordinate-converted into a shape adhering to ultrasonic scanning.

In addition, a B-mode image (ultrasonic cross-sectional image) signal (B-mode signal) is supplied from an envelope detecting unit 9 to DSC 8, in the same way, and the DSC 8 not only coordinate-converts the supplied image data into a shape adhering to ultrasonic scanning, but also combines B-mode signal and blood flow information and shows a two-dimensional blood flow image on a monitor 10.

The blood flow velocity data comprised in the blood flow information is data which has a possibility of generating an aliasing phenomenon based on the Nyquist theorem. With regards to this measurement of blood flow velocity data having this aliasing, a method, for example, for performing filter processing with an arbitrary order after determining aliasing and performing corrections is disclosed in the following Patent Document 1 as a method for filter processing in filter 7.

Patent Document 1: Japanese Patent Application Publication No. 4-161146 (Heisei)

DISCLOSURE OF THE INVENTION

Problems to be Solved by the Invention

However, in the filter processing method for blood flow velocity data disclosed in Patent Document 1, the aliasing determination method and the aliasing correction method are complicated, and this is problematic in that, in order to actualize this filter processing method, a complicated hardware configuration is required.

In light of the foregoing problems, an object of the present invention is to provide an ultrasonic Doppler blood flow measuring device which actualizes the filtering of blood flow velocity data having aliasing and performing a screen display of blood flow velocity which changes smoothly, spatially and temporally.

Means for Solving the Problem

In order to achieve the foregoing object, the ultrasonic Doppler blood flow measuring device of the present invention has a blood flow velocity filter means for performing filter processing in order to calculate the blood flow velocity value of the blood within a subject biological body from the echo signals of ultrasonic pulse transmitted to the subject biological body, wherein the blood flow velocity filter means comprises:

a difference calculating means for subtracting the focus point blood flow velocity value of an arbitrary focus point from the blood flow velocity value supplied to the blood flow velocity filter means and calculating the difference value thereof;

a filter means for performing filter processing on the difference values; and an addition processing means for adding the focus point blood flow velocity value to the filter processing result from the filter means.

According to this configuration, it becomes possible to perform filter processing of blood flow velocity data which has aliasing by only common filter means and common addition and subtraction means, and a smooth image display of blood flow velocity can be actualized.

Furthermore, the ultrasonic Doppler blood flow measuring device of the present invention is configured such that the difference calculating means calculates the difference value of consecutive point blood flow velocity value of a point which is spatially consecutive to the arbitrary focus point and the arbitrary focus point blood flow velocity value.

According to this configuration, when performing an image display of the blood flow velocity of the blood flowing within the subject biological body, it becomes possible to reduce spatial random noise within one image frame and a smooth image display of blood flow velocity can be actualized.

Furthermore, the ultrasonic Doppler blood flow measuring device of the present invention is configured such that the difference calculating means calculates the difference value of the blood flow velocity value which is temporally consecutive to the arbitrary focus point and the arbitrary focus point blood flow velocity value.

According to this configuration, when performing an image display of the blood flow velocity of the blood flowing within the subject biological body, it becomes possible to reduce temporal random noise between a plurality of image frames and a smooth image display of blood flow velocity can be actualized.

Advantageous Effects of the Invention

The ultrasonic Doppler blood flow measuring device of the present invention has a blood flow velocity filter means for performing filter processing to calculate the blood flow velocity value of the blood flowing within the subject biological body from the echo signals of the ultrasonic pulse transmitted to the subject biological body, wherein the blood flow velocity filter means comprises a difference calculating means for subtracting the focus point blood flow velocity value of an arbitrary focus point from the blood flow velocity value supplied to the blood flow velocity filter means and calculates the difference value thereof, a filter means for performing filter processing on the difference value, and an addition processing means for adding the focus point blood flow velocity value to the filter processing result from the filter means, and has an effect, wherein the filter processing of blood flow velocity data which has aliasing is preformed by only common filter means and common addition and subtraction means, and a smooth image display of blood flow velocity is actualized.

BEST MODE FOR CARRYING OUT THE INVENTION

An ultrasonic Doppler blood flow measuring device according to first and second embodiments of the present invention is described hereafter, with reference to the drawings.

First Embodiment

Figure 1:
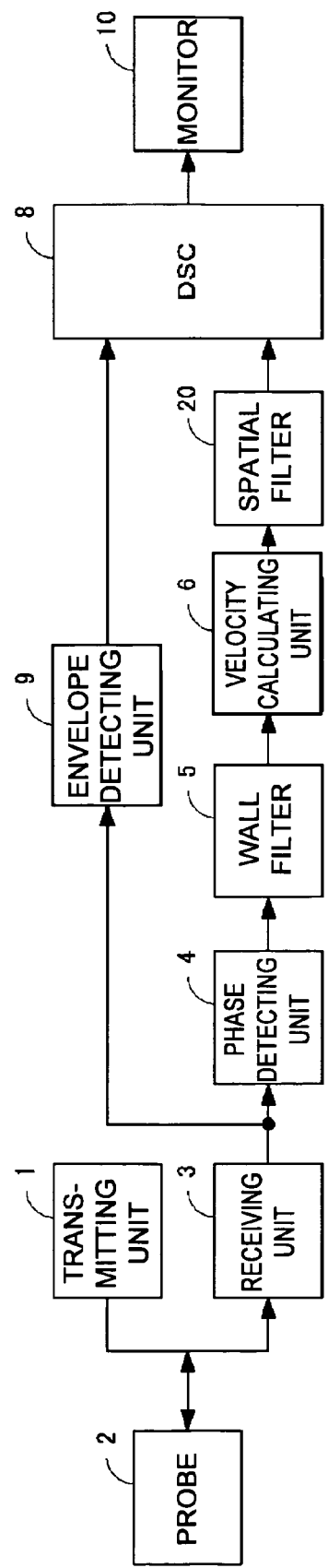
[FIG. 1] A block diagram showing a configuration of an ultrasonic Doppler blood flow measuring device according to a first embodiment of the present invention.
Figure 5:
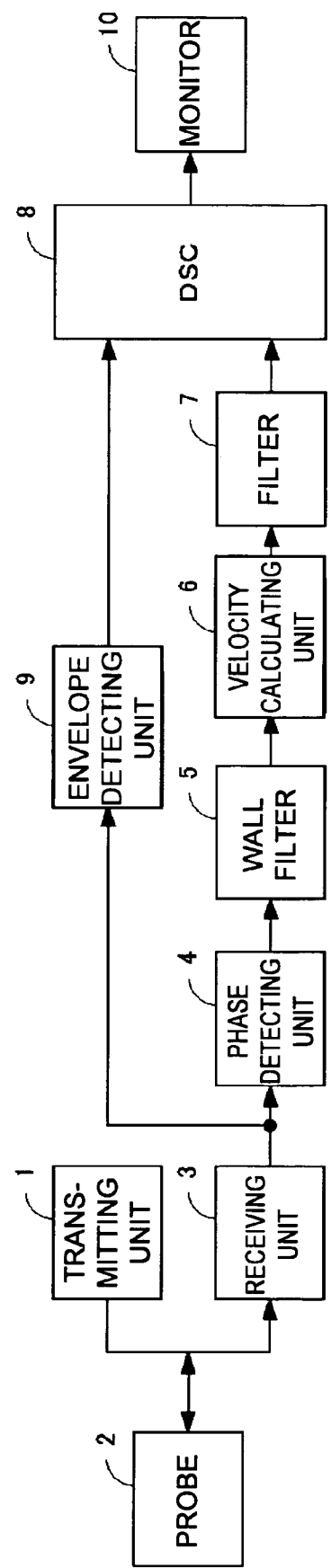
[FIG. 5] A block diagram showing one example of a configuration of an ultrasonic Doppler blood flow measuring device according to prior art.

First, the first embodiment of the present invention is described. FIG. 1 is a block diagram showing a configuration of an ultrasonic Doppler blood flow measuring device according to the first embodiment of the present invention. The ultrasonic Doppler blood flow measuring device shown in FIG. 1 comprises a transmitting unit 1, a probe 2, a receiving unit 3, a phase detecting unit 4, a wall filter 5, a velocity calculating unit 6, a digital scan converter (DSC) 8, an envelope detecting unit 9, and a monitor 10. Although the ultrasonic Doppler blood flow measuring device shown in FIG. 1 has almost the same configuration as the ultrasonic Doppler blood flow measuring device shown in FIG. 5, a spatial filter 20 is provided in place of the filter 7. In the ultrasonic Doppler blood flow measuring device shown in FIG. 1, the constituent elements excluding the spatial filter 20 are the same as the constituent elements of the conventional ultrasonic Doppler blood flow measuring device shown in FIG. 5, the same reference numbers are cited and explanations of operations are omitted, as well.

Figure 2:
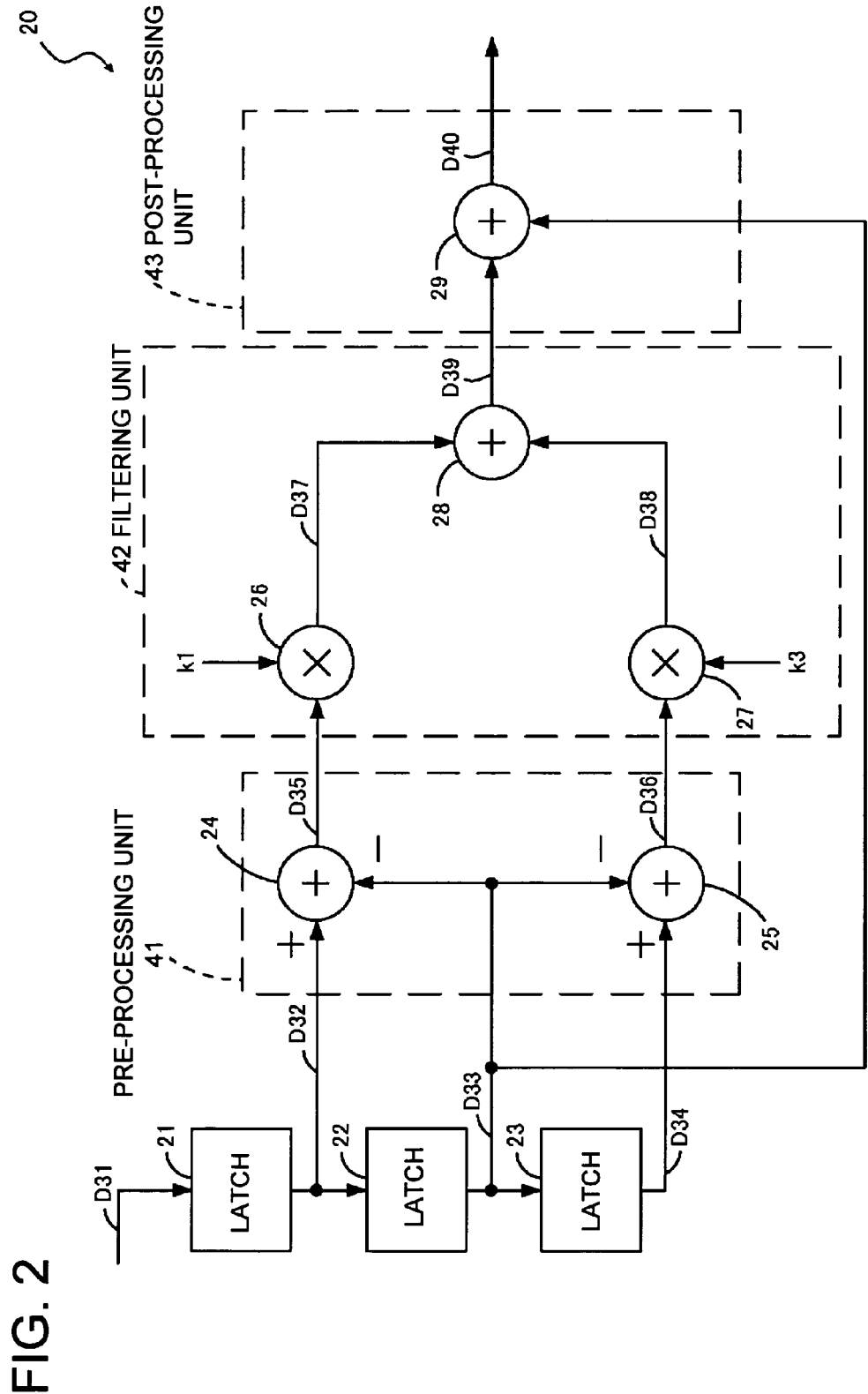
[FIG. 2] A block diagram showing a detailed configuration of a spatial filter of the ultrasonic Doppler blood flow measuring device according to the first embodiment of the present invention.

FIG. 2 is a block diagram showing a detailed configuration of the spatial filter of the ultrasonic Doppler blood flow measuring device according to the first embodiment of the present invention. The spatial filter 20 shown in FIG. 2 comprises latches 21, 22, and 23 which can hold data, adders 24, 25, 28, and 29 which can add or subtract two data, and multipliers 26 and 27 which can multiply two data. The adders 24 and 25 comprise a pre-processing unit (difference calculating unit) 41, the multipliers 26 and 27 and the adder 28 comprise a filtering unit 42, and the adder 29 comprises a post-processing unit (addition processing unit) 43.

The connection configuration of respective constituent elements within the spatial filter 20 shown in FIG. 2 and the flow of data are described hereafter. Latches 21, 22, and 23 are placed in order to hold data (blood flow velocity value) of a plurality of focus points spatially consecutive in the acoustic scan line of ultrasound. The input signal (blood flow velocity value) D31 of the blood flow information from the velocity calculating unit 6 is provided to the latch 21. This input signal D31 includes data on an arbitrary focus point, namely, when measuring, the input signal (consecutive point blood flow velocity value) D31 of focus points spatially consecutive in the acoustic scan line of ultrasound is provided continuously, and the input signal D31 from the velocity calculating unit 6 is provided continuously to the latch 21. When the input signal D31 is provided from the velocity calculating unit 6, the latch 21 holds the input signal D31 and provides the held data (for example, data of the previous focus point) D32 to the latch 22 and the adder 24, as well.

When data D32 provided from the latch 21 is provided, the latch 22 also holds this data D32 and provides the held data (for example, data of the previous focus point) D33 to the latch 23 and the adder 24, 25, and 29, as well. Furthermore, when data D33 provided from the latch 22 is provided, the latch 23 also holds this data D33 and provides the held data D34 to the adder 25. In this way, data D32, D33, and D34 of spatially consecutive focus points are output to the pre-processing unit 41 at the same timing from the latches 21, 22, and 23, respectively.

In addition, between the latches 21, 22, and 23 and the adders 24 and 25, the output of the latch 21 is connected to the input on the addition side of the adder 24, the output of the latch 22 is connected to the input of the subtraction sides of the adder 24 and 25, respectively, and the output of the latch 23 is connected to the input on the addition side of the adder 25. In this way, the adder 24 receives data D32 from the addition side and data D33 from the subtraction side, respectively, performs calculation, and outputs the result of subtracting data D33 from data D32 to the multiplier 26 as data D35. In addition, the adder 25 receives data D34 from the addition side and data D33 from the subtraction side, respectively, performs calculation, and outputs the result of subtracting data D33 from data D34 to the multiplier 27 as data D36.

The multipliers 26 and 27 multiply the provided data by the filter coefficients set respectively to the provided data and outputs the results. Therefore, the multiplier 26 multiplies filter coefficient k1 and data D35 provided from the adder 24 and outputs data D37, and the multiplier 27 multiplies filter coefficient k3 and data D36 provided from the adder 25 and outputs data D38. The adder 28 receives data D37 and D38 from the multipliers 26 and 27, adds these data, and outputs the added result to the adder 29 as data D39. Then, the adder 29 receives data D33 from the latch 22 and data D39 from the adder 28, respectively, adds these data, and outputs the added result to the DSC 8 as data D40.

The spatial filter 20 according to the present embodiment is a one-dimensional filter and a second order filter. In other words, in the present embodiment, the focus sample data D33 is subtracted from the consecutive point blood flow velocity value (data D32 and D34), which is consecutively before and after the focus point. Data D35 and D36, where focus sample data D33 is the origin (in other words, 0), are created by the pre-processing unit 41 composed of adders 24 and 25, with the focus point as data (focus sample data or focus point blood flow velocity value) D33 which is output from the latch 22.

The pre-processing unit 41, the filtering unit 42, and the post-processing unit 43 operate as a second order FIR (Finite duration Impulse Response) filter, by the combination thereof.

The filter operation of the present invention is described using equations.

If output data D40 is expressed using respective data in FIG. 2,
[Equation 1]

$$D40=D39+D33$$

$$D40=D37+D38+D33$$

$$D40=k1*D35+k3*D36+D33$$

$$D40=k1*(D32-D33)+k3*(D34-D33)+D33$$

$$D40=k1*D32+(1-k1-k3)*D33+k3*D34 \quad \text{Equation 1}$$

From equation 1, FIG. 2 can be considered a second order FIR filter having the following transfer function H(z).
[Equation 2]

$$H(z)=k1+(1-k1-k3)z^{\wedge}(-1)+k3z^{\wedge}(-2) \quad \text{Equation 2}$$

Here, $z^{\wedge}(-n)$ is an operator indicating the lag element of n column.

This FIR filter is given low-pass filter characteristics in order to eliminate random noise having high-frequency component. Therefore, as the second order FIR filter, it is preferable that all coefficients are positive numbers,
and are set to:
[Equation 3]

$$\phi<k1, \phi<k3, \text{ and } k1+k3<1 \quad \text{Equation 3}$$

In addition, the adders 24 and 25 perform, for example, a fixed decimal point calculation, the output data format is the same as the input data format, and the carry bit of the addition result is omitted (ignored). For example, if the input has an 8-bit 2's complement format, the output also has an 8-bit 2's complement format. Thus, data D35 is calculated as the difference value of data D32 and focus sample data D33, under the condition that the velocity difference between data is a smaller velocity difference than the velocity difference which causes aliasing. Similarly, data D36 is calculated as the difference value of data D34 and focus sample data D33, under the condition that the velocity difference between data is a smaller velocity difference than the velocity difference which causes aliasing.

By the foregoing processing, it becomes possible to perform filter calculation of the consecutive point blood flow value (three data D32, D33, and D34) provided to the second order FIR filter, with one data among these as the focus sample data (for example, data D33), under the assumption that the velocity difference between the blood flow velocity value of the focus sample data and the blood flow velocity data of other data is a smaller velocity difference than the velocity difference which causes aliasing. Therefore, at the same time (within the same image), after the difference value of an arbitrary center pixel is filter processed, it becomes possible to, again, add data on the arbitrary center pixel and obtain data on the desired blood flow velocity value, and spatial random noise can be reduced. Although the foregoing first embodiment was an example actualizing a one-dimensional second order filter, it is possible make an extension to a one-dimensional and two-dimensional, high-order filter, in the same way.

As described above, according to the ultrasonic Doppler. blood flow measuring device according to the first embodiment of the present invention, by providing the spatial filter 20 having the pre-processing unit 41 for performing subtraction with the focus sample data D33 as the origin and the filtering unit 42 for performing filter processing on all provided data, and the post-processing unit 43 for adding the focus sample data D33 to the output data D39 after filter processing by the filtering unit 42, it becomes possible to perform filter processing of blood flow velocity data (consecutive point blood flow velocity value) which are spatially consecutive in the acoustic scan line of ultrasound, without being influenced by aliasing, and a spatially smooth blood flow velocity image can be provided.

Second Embodiment

Figure 3:
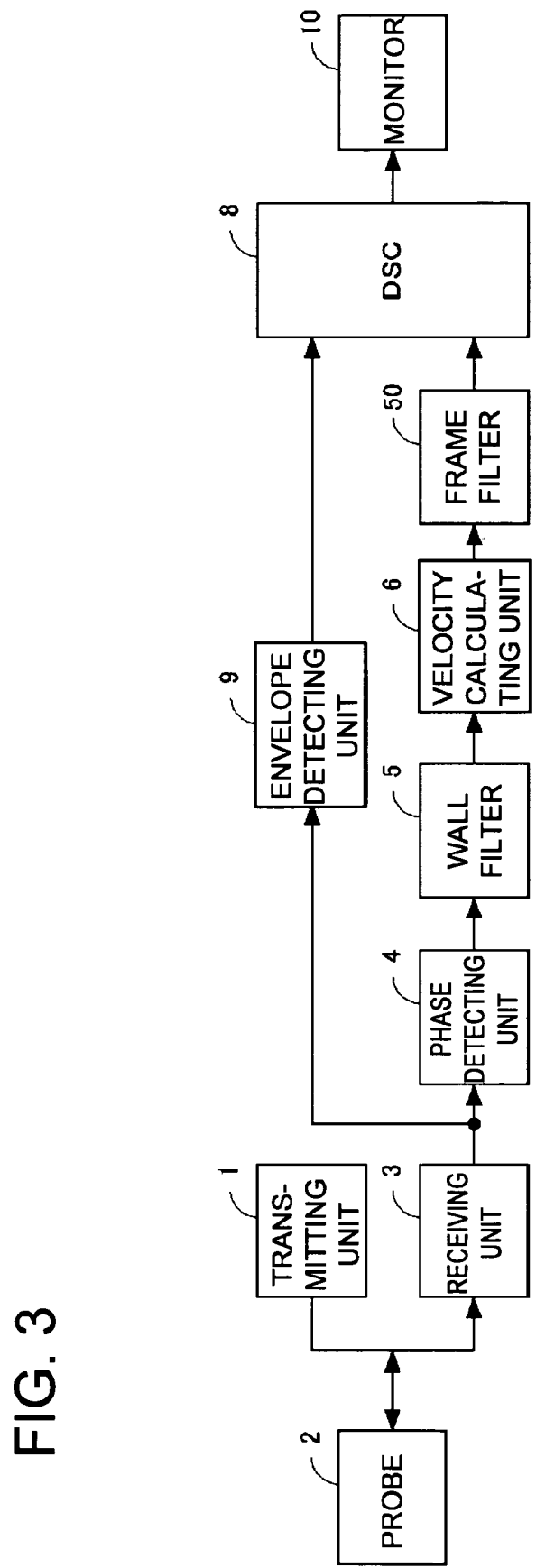
[FIG. 3] A block diagram showing a configuration of an ultrasonic Doppler blood flow measuring device according to a second embodiment of the present invention.

Next, a second embodiment of the present invention is described. FIG. 3 is a block diagram showing a configuration of the ultrasonic Doppler blood flow measuring device according to the second embodiment of the present invention. The ultrasonic Doppler blood flow measuring device according to the second embodiment of the present invention shown in FIG. 3 differs in that a frame filter 50 is provided in place of the spatial filter 20, held by the ultrasonic Doppler blood flow measuring device according to the first embodiment of the present invention. In the ultrasonic Doppler blood flow measuring device shown in FIG. 3, the constituent elements excluding the frame filter 50 are the same as the constituent elements of the conventional ultrasonic Doppler blood flow measuring devices shown in FIG. 1 and FIG. 5, the same reference numbers are cited and explanations of operations are omitted, as well.

Figure 4:
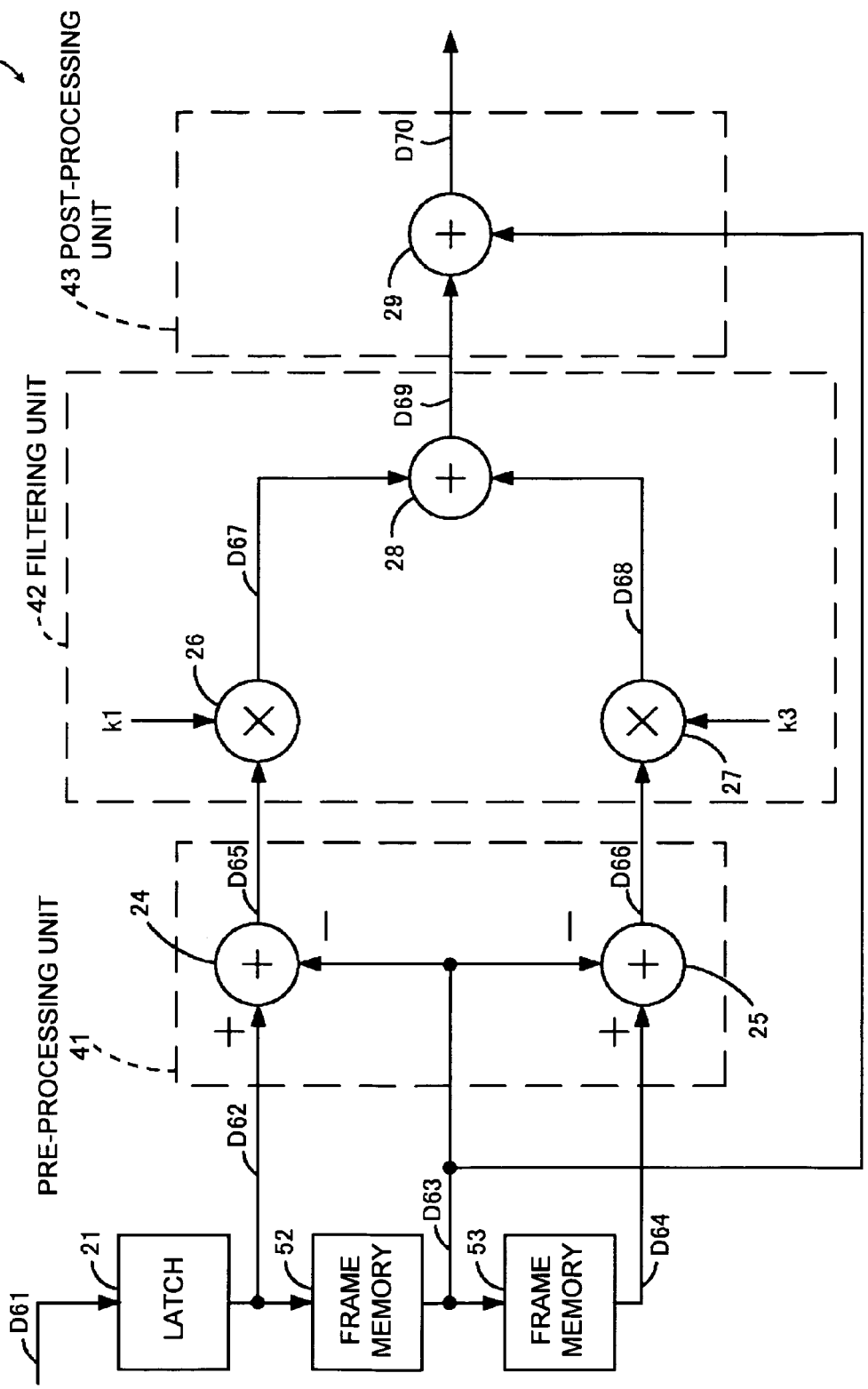
[FIG. 4] A block diagram showing a detailed configuration of a frame filter of the ultrasonic Doppler blood flow measuring device according to the second embodiment of the present invention.

FIG. 4 is a block diagram showing a detailed configuration of the frame filter of the ultrasonic Doppler blood flow measuring device according to the second embodiment of the present invention. The frame filter 50 shown in this FIG. 4 differs in that, in comparison with the spatial filter 20 shown in FIG. 2, frame memories 52 and 53 are provided in place of latches 22 and 23. In the frame filter 50 shown in FIG. 4, the constituent elements excluding the frame memories 52 and 53 are the same as the constituent elements of the spatial filter 20 shown in FIG. 2, the same reference numbers are cited and explanations of operations are omitted, as well.

The connection configuration of respective constituent elements within the frame filter 50 shown in FIG. 4 and the flow of data are described. The input signal D61 of the blood flow information from the velocity calculating unit 6 is provided to the latch 21. This input signal 61 includes data on an arbitrary focus point, namely, when measuring, the input signal (blood flow velocity value) D61 of focus points which are consecutive in the acoustic scan line of ultrasound is provided continuously, and the input signal D61 from the velocity calculating unit 6 is provided continuously to the latch 21. When the input signal D61 is provided from the velocity calculating unit 6, the latch 21 holds the input signal D61 and provides the held data (for example, data of the previous focus point) D62 to the frame memory 52 and the adder 24, as well.

After the input signal D61 of the blood flow information from the velocity calculating unit 6 is provided to the latch 21, the signal is further provided to the frame memory 52 as data D62. The frame memory 52 holds data D62 provided from the latch 21 and outputs data D63 of the one frame prior thereto in the same region, as well. In addition, the frame memory 53 similarly holds data D63 output from the frame memory 52 and outputs data D64 of the one frame prior thereto in the same region (two frames before data D62), as well. Thus, data D62, D63, and D64 of the same region within temporally consecutive frames (in other words, blood flow velocity values temporally consecutive to the arbitrary focus point) are output to the pre-processing unit 41 at the same timing from the latch 21 and the frame memories 52 and 53, respectively. In this case, data D63 is used as the focus sample data (focus point blood flow velocity value), and the same processing as that in the foregoing first embodiment is performed in the pre-processing unit 41, the filtering unit 42, and the post-processing unit 43.

By the foregoing processing, it becomes possible to perform filter calculation of the three data, D62, D63, and D64, provided to the second order FIR filter, with one data among these as the focus sample data (for example, data D63), under the assumption that the velocity difference between the blood flow velocity value of the focus sample data and the blood flow velocity data of other data is a smaller velocity difference than the velocity difference which causes aliasing. Therefore, after the difference value of data on the blood flow velocity value at an arbitrary time and the data on the blood flow velocity value which is temporally prior and subsequent thereto is filter processed, in the same region, it becomes possible to, again, add data on the blood flow velocity value at a predetermined time and obtain data on the desired blood flow velocity value, and temporal random noise between a plurality of temporally consecutive images can be reduced.

As described above, according to the ultrasonic Doppler blood flow measuring device according to the second embodiment of the present invention, by providing the frame filter 50 having the pre-processing unit 41 for performing subtraction with the focus sample data D63 as the origin and the filtering unit 42 for performing filter processing on all provided data, and the post-processing unit 43 for adding the focus sample data D63 to the output data after filter processing by the filtering unit 42, it becomes possible to perform filter processing of blood flow velocity data (blood flow velocity value temporally consecutive to arbitrary focus point) which are temporally consecutive in the same region in the acoustic scan line of ultrasound without being influenced by aliasing, and a temporally smooth blood flow velocity image can be provided. Although the foregoing second embodiment was an example actualizing a second order frame filter, it is possible make an extension to a filter of a higher order, in the same way.

Although the frame filter 50 is provided between the velocity calculating unit 6 and the DSC 8 in the foregoing second embodiment, it can be provided between the DSC 8 and the monitor 10, as well. In addition, although the ultrasonic Doppler blood flow measuring device having the spatial filter 20 was described in the first embodiment and the ultrasonic Doppler blood flow measuring device having the frame filter 50 was described in the second embodiment, separately, it is also possible to provide both the spatial filter 20 and the frame filter 50 within the ultrasonic Doppler blood flow measuring device. Furthermore, although the spatial filter 20 and the frame filter 50 are configured by hardware in the first and second embodiments, the filter processing performed by these filters can also be actualized by software programs.

INDUSTRIAL APPLICABILITY

The ultrasonic Doppler blood flow measuring device according to the present invention can actualize filtering of blood flow velocity data having aliasing by a simple, small-scale algorithm and perform image display of blood flow velocity which changes smoothly, spatially or temporally, and in the medical field, can be applied to technology for measuring the blood flow within a biological body sing the Doppler phenomenon of the ultrasonic waves and performing image display related to this measured result, as well as, in particular, applied to technology for color-displaying image of blood flow velocity data generated by the aliasing phenomenon.

The invention claimed is:

1. An ultrasonic Doppler blood flow measuring device, comprising: a velocity calculating unit for calculating a blood flow velocity value of a blood within a subject biological body from a Doppler-shift detected from echo signals of ultrasonic pulses transmitted to said subject biological body; and
   a blood flow velocity filter means for performing filter processing of said blood flow velocity value outputted from said velocity calculating unit without being influenced by aliasing, wherein
   the blood flow velocity filter means comprises:
      a first difference calculating means for subtracting a first blood flow velocity value of a first focus point adjacent to an arbitrary focus point supplied to said blood flow velocity filter means from a blood flow velocity value of said arbitrary focus point supplied to said blood flow velocity filter means and calculating a first difference value thereof;
      a second difference calculating means for subtracting said blood flow velocity value of said arbitrary focus point supplied to said blood flow velocity filter means from a second blood flow velocity value of a second focus point adjacent to said arbitrary focus point supplied to said blood flow velocity filter means and calculating a second difference value thereof;
      a filter means for performing filter processing on said first and second difference values; and
      an addition processing means for adding said blood flow velocity value of said arbitrary focus point to a filter processing result from said filter means,
      wherein said filter means comprises:
         a first multiplier for multiplying said first difference value by a coefficient;
         a second multiplier for multiplying said second difference value by a coefficient; and
         an adder for adding outputted data from said first and second multipliers, and
      wherein said first and second difference calculating means and said adder perform a fixed decimal point calculation.

2. The ultrasonic Doppler blood flow measuring device according to claim 1, wherein said first focus point, said arbitrary focus point and said second focus point are spatially consecutive.

3. The ultrasonic Doppler blood flow measuring device according to claim 1, wherein said first focus point, said arbitrary focus point and said second focus point are temporally consecutive.

* * * * *